United States Patent [19]
Frankel et al.

[11] Patent Number: 5,314,072
[45] Date of Patent: May 24, 1994

[54] SORTING PLASTIC BOTTLES FOR RECYCLING

[75] Inventors: Henry Frankel, Edison; Sergey Miroshnichenko, Highland Park; Jonathan B. Whitlock, Warren, all of N.J.

[73] Assignee: Rutgers, The State University, Piscataway, N.J.

[21] Appl. No.: 939,304

[22] Filed: Sep. 2, 1992

[51] Int. Cl.⁵ .............................................. B07C 5/342
[52] U.S. Cl. .................................. 209/44.1; 209/522; 209/524; 209/580; 209/588; 209/589
[58] Field of Search ................ 209/12, 44.1, 524, 522, 209/577, 580, 581, 582, 585, 588, 589, 938

[56] References Cited

U.S. PATENT DOCUMENTS

| | | | |
|---|---|---|---|
| 2,627,975 | 2/1953 | Ekstrom et al. | 209/111 |
| 3,358,552 | 12/1967 | Schneider | 88/14 |
| 3,747,755 | 7/1973 | Senturia et al. | 209/577 |
| 3,890,221 | 6/1975 | Muehlethaler | 209/577 |
| 3,975,261 | 8/1976 | Beck | 209/74 M |
| 4,017,194 | 4/1977 | Conroy et al. | 356/240 |
| 4,224,350 | 9/1980 | Merck | 426/473 |
| 4,248,389 | 2/1981 | Thompson et al. | 241/101.5 |
| 4,438,851 | 3/1984 | Voelskow | 209/616 |
| 4,541,532 | 9/1985 | Wilson | 209/651 |
| 4,848,590 | 7/1989 | Kelly | 209/564 |
| 4,858,768 | 8/1989 | Plester | 209/3.1 |
| 4,919,534 | 4/1993 | Reed | 209/582 |
| 5,024,335 | 6/1991 | Lundell | 209/618 |
| 5,141,110 | 8/1992 | Trischan et al. | 209/524 |

FOREIGN PATENT DOCUMENTS

| | | |
|---|---|---|
| 0007248 | 1/1980 | European Pat. Off. |
| 0263015 | 4/1988 | European Pat. Off. |
| 0291959 | 11/1988 | European Pat. Off. |
| 0441012 | 8/1991 | European Pat. Off. |
| 3445428 | 6/1986 | Fed. Rep. of Germany |
| 3528069 | 2/1987 | Fed. Rep. of Germany |
| 3731402 | 12/1988 | Fed. Rep. of Germany |
| 3905231 | 8/1990 | Fed. Rep. of Germany |
| 56-145339A | 11/1981 | Japan |
| 1520858 | 8/1978 | United Kingdom |

OTHER PUBLICATIONS

Press release, Eaglebrook Plastics, Inc. (Aug. 23, 1991).
Handout excerpt, "RETEC-Recycling Technology of the '90s" (Nov. 29-30, 1990).
Frankel, Henry: entry to the "Masters of Innovation Competition," (about Feb. 1989).

*Primary Examiner*—D. Glenn Dayoan
*Assistant Examiner*—Dean A. Reichard
*Attorney, Agent, or Firm*—Lerner, David, Littenberg, Krumholz & Mentlik

[57] ABSTRACT

An apparatus and method for sorting plastic bottles for recycling wherein if it is first determined that a bottle is clear, the bottle will be ejected. If the bottle is not determined as being clear, the apparatus or method next determines if the bottle is colored. If the bottle is colored, the bottle will be ejected. The above method may also be accomplished by use of a truth table which analyzes the characteristics of a bottle. Also provided is a detector for detecting the presence of chlorine in a plastic bottle by means of X-ray fluorescence. A sorter device sorts the bottles into small diameter and large diameter bottles.

23 Claims, 7 Drawing Sheets

SORTING PLASTIC BOTTLES FOR RECYCLING

BACKGROUND OF THE INVENTION

This invention pertains to apparatus and methods for sorting plastic bottles for recycling.

The marketability of presorted plastic bottles is significantly greater than the marketability of unsorted plastic bottles. Thus, it is advantageous to sort plastic bottles for recycling into marketable categories. Sortation of plastic beverage and household containers has been performed manually, which is a labor intensive, expensive, and often inaccurate process. As recycling efforts in communities increase, so does the need for a faster and more efficient recycling sorting method.

Various arrangements have been proposed for accomplishing these tasks. Reed, U.S. Pat. No. 4,919,534, sorts returned glass and PET bottles by testing the material with polarized and colorized light. Alternately flashing red and green polarized light is optically detected as the light passes through the bottle. The rotation of the polarized light differentiates between glass and PET.

Plester, U.S. Pat. No. 4,858,768, removes plastic bottles which have been contaminated previous to their arrival at the sorting center. Warm water is injected into the plastic bottle, agitated, and various residue analyzers determine the characteristics of the residue. For example, electromagnetic radiation, light scattering, polarized light rotation, and X-ray fluorescence may be used to examine the residue.

Thompson et. al, U.S. Pat. No. 4,248,389, discloses a detector which sorts recycled bottles by scanning the Universal Product Code, using that code to classify the bottle, and sorting the bottle into the appropriate bin for later reclamation.

Schneider, U.S. Pat. No. 3,358,552, discloses sorting bottles by optically determining the placement of a label, the color of the bottle, and the pattern engraved in the glass. The outlets of these sensors are fed into a logic circuit, which then determines the commercial affiliation of the bottle by determining the combination of the triggered detectors.

Kelly, U.S. Pat. No. 4,848,590, discloses sorting different types of scrap metal on the basis of their X-ray fluorescence. Depending on the type of metal detected, the metal is directed to various storage areas.

Japanese Patent No. 56145339 generally discloses detecting chlorine in a vinyl chloride resin to determine the degree of aging of the resin.

Lundell, U.S. Pat. No. 5,024,335, discloses a mechanical sorter for removing large plastic containers and aluminum cans from other refuse. A variety of refuse is transported below rotating brushes. Those containers which are too large to fit under the brushes are lifted off the conveyors and over the top of the brushes. After the containers pass over the top of the brushes, they are diverted to a separate conveyor for later removal.

Despite all of this effort toward the development of recycling methods and apparatus, there are needs for further improvement.

SUMMARY OF THE INVENTION

The present invention provides systems and methods for sorting bottles for recycling which meet those needs.

One aspect of the present invention provides a method whereby a bottle is conveyed via a conveying means to a first sensing area, where it is determined whether the bottle is clear transparent, and if the bottle is clear, the bottle is removed from the conveying means to a pile of clear transparent bottles. If the bottle is not removed in this clear sensing area, the bottle is conveyed via the conveying means to a second, separate sensing area, where it is determined whether the bottle is tinted transparent. If the bottle is tinted transparent, it is removed from the conveying means to a pile of tinted transparent bottles.

Preferably, a third separate sensing area is included, where it is determined whether the bottle is translucent, and if the bottle is translucent, the bottle is removed to a pile of translucent bottles.

The opaque bottles pass all previous sensing areas undiverted and are removed to a pile of opaque bottles at the end of conveyor.

Each step of determining whether a bottle has a certain characteristic preferably includes disposing the bottle between a light emitter and a light detector, passing the light through the bottle, and determining if the magnitude of the light has diminished by passage through the bottle. For example, the first sensing area, which determines whether the bottle is clear, uses red light. The second sensing area uses light of a wavelength corresponding to a particular color to detect the presence of that color. Preferably, that particular color is green. As for the third sensing area, a high intensity red light is used. By sorting bottles in this order, green bottles may pass through the first sensing area without being removed, and translucent bottles may pass through the first and second sensing areas without being removed.

Other sensing areas may be added before the first, second or third sensing area, which can detect whether the bottle is glass or PVC.

For example, one aspect of this invention includes a polarization sensing area which determines whether the bottle is glass or PVC when the bottle is in the polarization sensing area, and if the bottle is glass or PVC, diverts that bottle from the line of conveyed bottles. To determine if the bottle is glass or PVC, the bottle is disposed between a circularly polarized light emitter and circularly polarized light detector, circularly polarized light is emitted and passed through the bottle, and it is then determined whether the light polarization has changed upon passage through the bottle. If the bottle does not change the polarization of light significantly then it is determined to be composed of glass or PVC. Another polarization bottle sensing area may separate the diverted glass bottles from the PVC bottles, or may be disposed behind the other polarization sensing area in series. Light polarization changes less upon passage through glass than upon passage through PVC.

Another aspect of this invention includes detecting the presence of chlorine in bottles to be recycled. A method in accordance with this aspect of the invention comprises the steps of irradiating a plastic bottle to be recycled with X-rays and detecting the secondary X-ray fluorescence associated with the presence of chlorine. Preferably, this method includes conveying a plurality of plastic bottles along a conveying means into a sensing area for detecting the presence of chlorine, and removing any of those bottles whose secondary X-ray fluorescence is associated with the presence of chlorine. The X-rays employed for irradiation may be about 6-KEV (Kiloelectron Volts) X-rays from a radioactive iron (Fe-55) source. The secondary radiation detected may be at about 2.8 KEV.

Preferred detection steps according to this aspect of the invention can detect the presence of polyvinyl chloride or polyvinylidine chloride in plastic bottles to be recycled.

Further, the step of detecting can also comprise measuring the secondary X-ray fluorescence of the bottles at predetermined intervals of time during each irradiating step, so that a plurality of measurements are performed with respect to each bottle. If the secondary X-ray fluorescence measured by at least one of these measurements is associated with the presence of chlorine, it is signalled that a bottle contains chlorine.

Another aspect of this invention includes detecting the presence of PVC, PVDC or glass bottles by use of circularly polarized light. This method comprises disposing a bottle between a first polarized light emitter and a first polarized light detector, emitting circularly polarized light and passing the light through the bottle, and determining whether this light has changed polarization by passage through the bottle. Further, it is preferable to convey one bottle from a line of bottles between the emitter and detector, and diverting the bottle to a pile of glass bottles if the change in polarization indicates the bottle is glass, and diverting the bottle to a pile of PVC or PVDC bottles if a change in polarization indicates that the bottle is composed of PVC or PVDC. Alternatively, the method further comprises conveying one bottle between the emitter and the detector from a line of bottles, and if the absence in change of polarization indicates that the bottle is glass, diverting the bottle to a pile of glass, but if the bottle is not diverted, then disposing the one bottle between a second polarized light emitter and a second polarized light detector, emitting circularly polarized light through the bottle, determining the change in the polarization of such light, and then diverting the bottle to a pile of PVC or PVDC bottles if a change in a circularly polarized light indicates the bottle is composed of PVC or PVDC. Additionally, it is preferable to pass the light leaving the emitter through a linear polarized filter and then through a quarterwave plate to produce circularly polarized light of first handedness, and when determining the change in polarization, passing the light leaving the bottle through a second quarterwave plate followed by a second linear polarizing filter, the relative orientation of the second quarter wave plate with respect to the second linear polarizing filter being such to only block light that is circularly polarized in the first handedness. It is also preferable to emit nonpolarized light of substantially equivalent wavelength to the polarized light, and comparing the change in the detected signal between the polarized light and the nonpolarized light through the bottle.

Yet another aspect of the invention provides a system for sorting bottles for recycling. This system comprises a chlorine sensing means which includes an X-ray emitter for irradiating bottles to be sorted with X-rays, a fluorescence detector for measuring the resultant fluorescence produced by such radiation of each bottle, and providing a chlorine signal for each bottle corresponding with the magnitude of the resultant fluorescence for that bottle. The system further comprises clarity sensing means comprising a light emitter for emitting light through the bottles, a light detector for determining the extent of transmission of the light through the bottle, and a clarity signal corresponding with the magnitude of the transmission of light through the bottles. Transparent tinted sensing means are also provided and comprise a colored light emitter for emitting light through the bottles, a light detector for determining the attenuation of that colored light through the bottles, and a color signal corresponding with the intensity of the transmitted light through each bottle. This system also comprises memory means containing predetermined values, and comparison means for comparing each chlorine, clarity and color signal with one of the predetermined values. Thus, a first comparison means creates a first resultant signal dependent upon the result of the comparison between the chlorine signal and a predetermined value. A second comparison means compares the clarity signal of each bottle with one of the predetermined values, and creates a second resultant signal for that bottle dependent upon the result of the comparison. A third comparison means compares the color signal of each bottle with one of the predetermined values, and creates a third resultant signal for that bottle dependent upon the result of the comparison. Means are also provided for defining a plurality of holding areas for receiving bottles for recycling, and each holding area corresponds with one type of bottle for recycling. This system also includes computation means for using all of the resultant signals to determine which of the holding areas should receive the bottle, and the computation means provides a holding area signal for each bottle indicating a particular one of the holding areas. Diversion means are also included for diverting the bottle into the appropriate holding area according to the holding area signal generated by the computation means for that bottle.

The above system preferably includes polarization sensing means comprising a polarized light emitter for emitting polarized light through each bottle, a polarized light detector for determining the extent of the change of such light through each bottle and a birefringent signal corresponding with whether the bottle is glass or PVC or not glass or PVC. A fourth comparison means is also included for comparing the birefringent signal of each bottle with one of the predetermined values and creating a fourth resultant signal for each bottle dependent upon the results of the bottle comparison. The computation means includes means for using the fourth resultant signal for each bottle in its determination.

Additionally, the system preferably includes translucent sensing means having a light emitter for emitting high intensity red light through the bottle, a detector for determining the extent of the attenuation of the high intensity red light through the bottles, and a translucent signal corresponding with the magnitude of the translucence of that bottle. Also included is a fifth comparison means for comparing the translucent signal of the bottle with one of the predetermined values, and creating a fifth resultant signal for the bottle depending on the result of the comparison. The computation means further includes means for using the fifth resultant signal for the bottle in its determination.

Preferably, the system includes a binary code image sensing system comprising a detector for determining if the bottle includes a binary code image containing a binary code, and providing a binary code signal for each bottle derived from the binary code. Also included is a sixth comparison means for comparing the binary code signal for each bottle with one of the predetermined values and creating a sixth resultant signal depending upon the results of the comparison, with the computation means including means for using the sixth resultant signal for each bottle in its determination. The binary code image is preferably a Universal Product Code. The comparison means and computation means are desirably contained in one digital computer.

Further, the system preferably includes bottle length sensing means comprising emitting light through each bottle, determining the attenuation of the light through the bottle, and providing a bottle length signal corresponding with the length of the bottle. Also included is a seventh comparison means for comparing the bottle length signal for each bottle with one of the predetermined values and creating a seventh resultant signal depending upon the results of the comparison, with the computation means including means for using the seventh resultant signal for each bottle in its determination. Preferably, the bottle length signal indicates attenuation of the emitted light, and the length of the bottle is determined by the length of time the bottle length signal indicates attenuation.

The bottle length signal may also be used to begin the emittance of light from the clarity sensing means, the color sensing means, the polarization sensing means, and the translucence sensing means, by beginning the emittance of the light from the above sensing means when the bottle length signal first indicates attenuation by the bottle to be sensed.

The diversion means comprises a plurality of individual diversion means. Each individual diversion means is associated with one of the plurality of holding areas and operates to divert the bottles from the conveyor to the associated holding area. The system further comprises an input conveyor for conveying a plurality of the bottles for recycling to the sensing means so that each bottle passes through all of the sensing means, and the plurality of bottles remain in a predetermined order whereby each of the sensing means provides a plurality of signals in an order corresponding to the order of the bottles.

The system can further comprise tracking means for allocating each chlorine signal, clarity signal, and color signal to one particular bottle. The tracking means might comprise bottle speed sensing means including a bottle speed detector for detecting the speed of the bottles on the conveyor, and a bottle speed signal corresponding with the speed of the bottle. The bottle speed signal is used by the tracking means.

In another aspect of the present invention, a system is provided to sort small diameter bottles and large diameter bottles. This system comprises a raw bottle storage means for holding mixed small diameter and large diameter bottles, a small bottle outlet means for discharging small diameter bottles, and a first conveyor means having an upper surface for moving bottles from the raw bottle storage means towards the small bottle outlet means while the bottles rest on the upper surface of the first conveyor means. A first ejector is also provided.

The first ejector is in association with means for moving the first ejector along a path spaced above the upper surface of the first conveyor means, this space being a first distance greater than the diameter of the small diameter bottles but less than the diameter of the large diameter bottles so that the first ejector will engage bottles on the first conveyor means protruding above the upper surface by more than this first distance before the bottles reach the small bottle outlet means. The first ejector diverts such bottles away from the small bottle outlet means. Also included is a second conveyor means having an upper surface for accepting bottles diverted by the first ejector and moving the bottles towards the raw bottle storage means while the bottles rest on the upper surface of the second conveyor means.

This system also comprises a second ejector means for moving the second ejector along a path spaced above the upper surface of the second conveyor means by a second distance greater than the diameter of the small diameter bottles but less than the diameter of the large diameter bottles so that the second ejector will engage any bottles on the second conveyor means which protrude above the upper surface by more than the second distance. The bottles will be engaged before they reach the raw storage bottles means and divert the bottles away from the raw bottle storage means. Finally, large bottle outlet means are included for discharging bottles diverted by the second ejector, whereby large bottles will be discharged through the large bottle outlet means and any small bottles ejected by the first ejector will be returned to the bottle storage means.

Preferably, the system also comprises an initial conveyor means adjacent to the small bottle outlet means. The initial conveyor means receives small diameter bottles and comprises a plurality of conveyors joined in series of increasing speed, with the lowest speed conveyor being closest to the small bottle outlet means. The initial conveyor means may also include walls on either side and bottle lining means for disposing the bottles in single file along one of the walls. The bottle lining means comprises a resilient arm means extending from one wall to spaced distance from the other wall.

Desirably, the first conveyor means has two ends and is inclined so that a first end is adjacent to the raw storage bottle means and is lower than the second end.

The path of the first ejector where it is closest to the first conveyor means preferably follows a direction opposite to the direction of the bottles resting on the first conveyor. Also, the path of the second ejector where it is closest to the second conveyor preferably follows a direction orthogonal to the direction of the bottles resting on the second conveyor.

The first ejector and second ejector may each comprise rotating cylinders with radially extending paddle means attached to the outer surface, such that the outermost edge of the paddle means follows the path of the ejector.

DETAILED DESCRIPTION OF THE PREFERRED EMBODIMENTS

Figure 1:
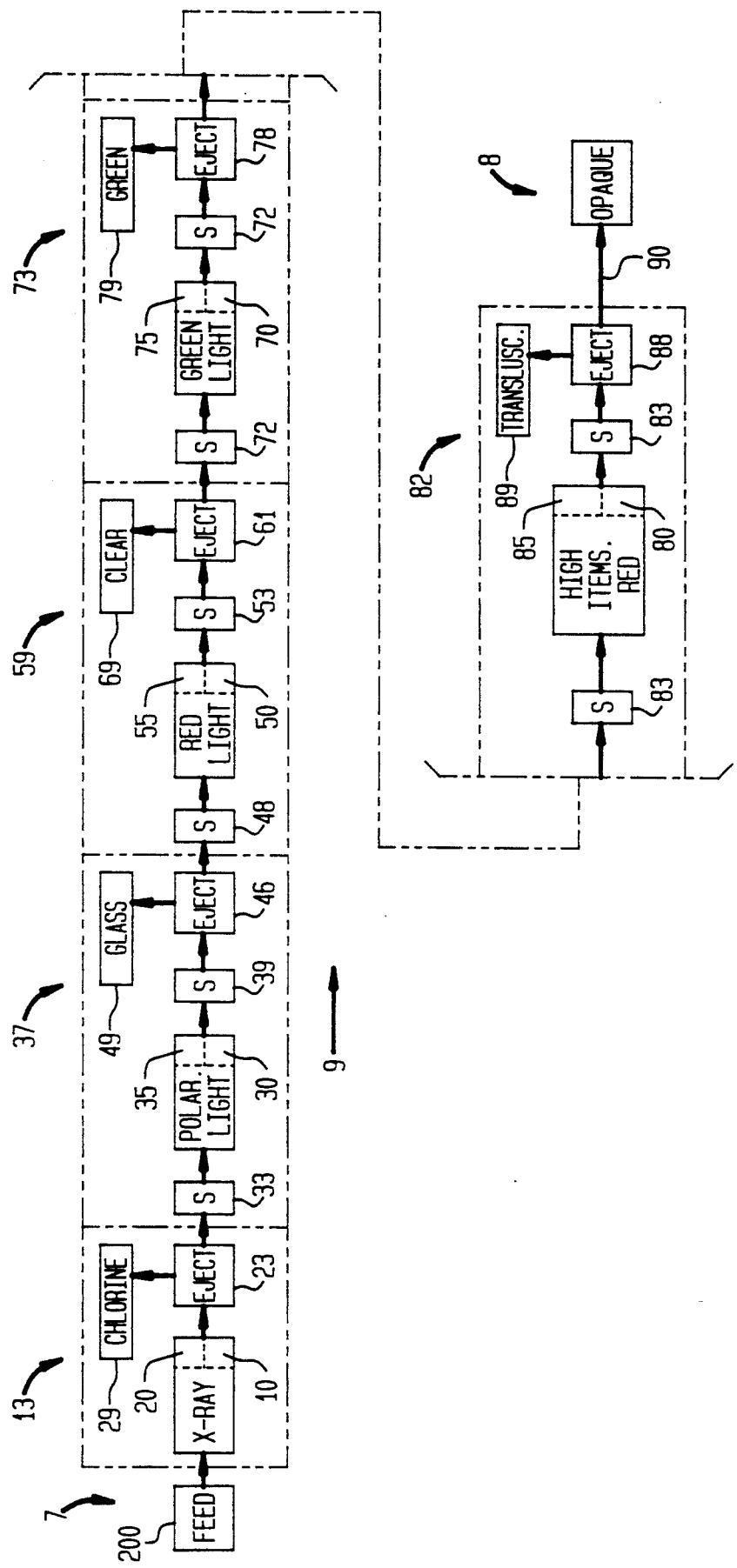
FIG. 1 is a block diagram of one of the preferred embodiments of the present invention.

In a system according to one embodiment of the invention, a feed mechanism 200 (FIG. 1) places bottles on a main conveyor which moves the bottles in a longitudinal direction 9. Bottles start at the beginning or "upstream" end 7 of the system, and travel in the direction 9 to a terminal or "downstream" end 8. Elements described as "downstream" of other elements in a system refers to the same direction of movement as the conveyor, and "upstream" refers to the opposite direction.

A variety of sensing areas are connected in series from beginning end 7 to terminal end 8. Adjacent to beginning end 7 is X-ray sensing area 13, which includes X-ray emitter 10 and detector 20, ejector 23, and chute 29. Immediately downstream of X-ray sensing area 13 is polarization sensing area 37. Polarization sensing area 37 includes presence detectors 33 and 39, polarized light emitter 30 and detector 35, ejector 46, and chute 49.

Adjacent and downstream of polarization sensing area 37 is clear bottle sensing area 59. Clear bottle sensing area 59 includes presence detectors 48 and 53, red light emitter 50 and detector 55, ejector 61 and chute 69. Immediately downstream of clear bottle sensing area 59 is green bottle sensing area 73 which includes presence detectors 72, green light emitter 70 and detector 75, ejector 78, and chute 79. Downstream of green bottle sensing area 73 is translucent bottle sensing area 82 which includes presence detectors 83, high intensity red light emitter 80 and detector 85, ejector 88 and chute 89. Downstream of all the sensing areas and adjacent terminal end 8 is chute 90.

This preferred embodiment is referred to as a multistation system, since there are multiple stations, each station consisting of a single sensing area and an associated single ejector immediately following the sensing area.

Figure 2:
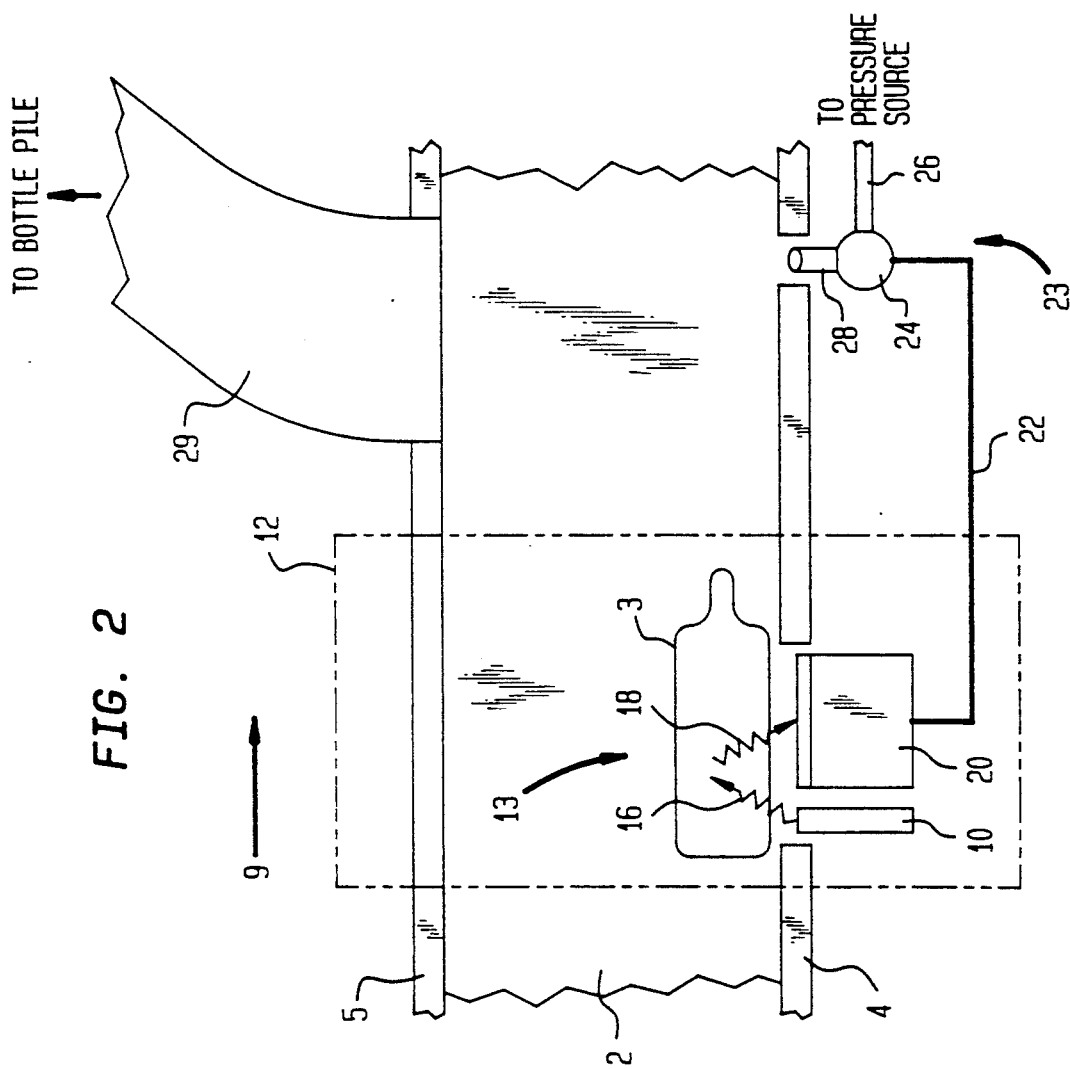
FIG. 2 is a plan view of the X-ray sensing area.

FIG. 2 illustrates a portion of the main conveyor 2 and the X-ray sensing area 13 in more detail. On either side of the conveyor 21, walls 4 and 5 rise above the upper surface of conveyor 2, and prevent bottles from falling off the sides. Preferably, conveyor 2 is at a slight incline, so that the side nearest wall 5 is higher than the side nearest wall 4. This incline causes bottles to gravitate towards wall 4 as they move down the conveyor. This is to bring the bottles as close as possible to the detection window of the PVC-detector. Because X-ray sensing area 13 detects chlorine, the conveyor itself should be made of substance which lacks chlorine, such as a silicone based material.

Bottles passing into X-ray sensing area 13 undergo an X-ray florescence test to detect the presence of chlorine in a passing bottle. X-ray emitter 10 is disposed on wall 4 and has a remote measuring head, which uses a 100 mCi sample of Fe-55 to provide 6-KEV X-rays to the sensing area. Alongside emitter 10 is X-ray detector 20 which measures the secondary radiation emitted by any item within the sensing area 13, but is calibrated to detect only secondary radiation equal to 2.8 KEV.

The output of detector 20 is digital, and is carried as an electrical current along output line 22. If chlorine has been detected, the current present on line 22 will be high, and if no chlorine is detected, the current will remain low or off. Line 22 is also connected to ejector 23, positioned along wall 4 and downstream of X-ray sensing area 13.

Ejector 23 includes a solenoid valve 24, a pressure source 26, and a blowout tube 28 having an outlet end at wall 4 directed substantially perpendicular to the direction of motion 9 of conveyor 2. If the current in line 22 is high, such as when chlorine has been detected, the tension of a spring contained within solenoid valve 24 is overcome, and air from pressure source 26 is diverted to blowout tube 28. Otherwise, the ejector remains unactivated, and no air exits through blowout tube 28. On the other side of conveyor 2 directly across from ejector 23 is chute 29. Chute 29 provides a break in wall 5, and is level with or below the upper surface area of conveyor 2. If air from pressure source 26 is diverted to blowout tube 28, an air blast will be directed across the conveyor from tube 28 to chute 29. Preferably, the pressure in pressure source 26 is 120 psi, which will provide an air stream of sufficient magnitude to divert any bottle 3 from wall 4 to chute 29. In some equipment configurations, it is desirable to have a second solenoid valve and blowout tube adjacent to and activated at the same time as the first. This effects more precise control over the trajectory of the ejected bottle and makes the trajectory less dependent on bottle size and mass. Chute 29 leads to a storage bin (not shown) for bottles containing chlorine.

Because ejector 23 is slightly downstream from X-ray sensing area 13, the ejector must stay on long enough for a bottle to travel from the sensing area and into the ejector's air stream. Therefore, the ejector is equipped with a delay mechanism (not shown), so that any time a bottle with chlorine is detected, the ejector stays on long enough for the bottle to enter the air stream and be diverted into chute 29.

For safety reasons, a plexiglass shield 12 surrounds the area irradiated by the X-ray emitter 10. This shield should be thick enough to prevent X-rays from escaping the area. Shield 12 has openings to allow bottles to enter and exit the irradiated area.

Figure 3:
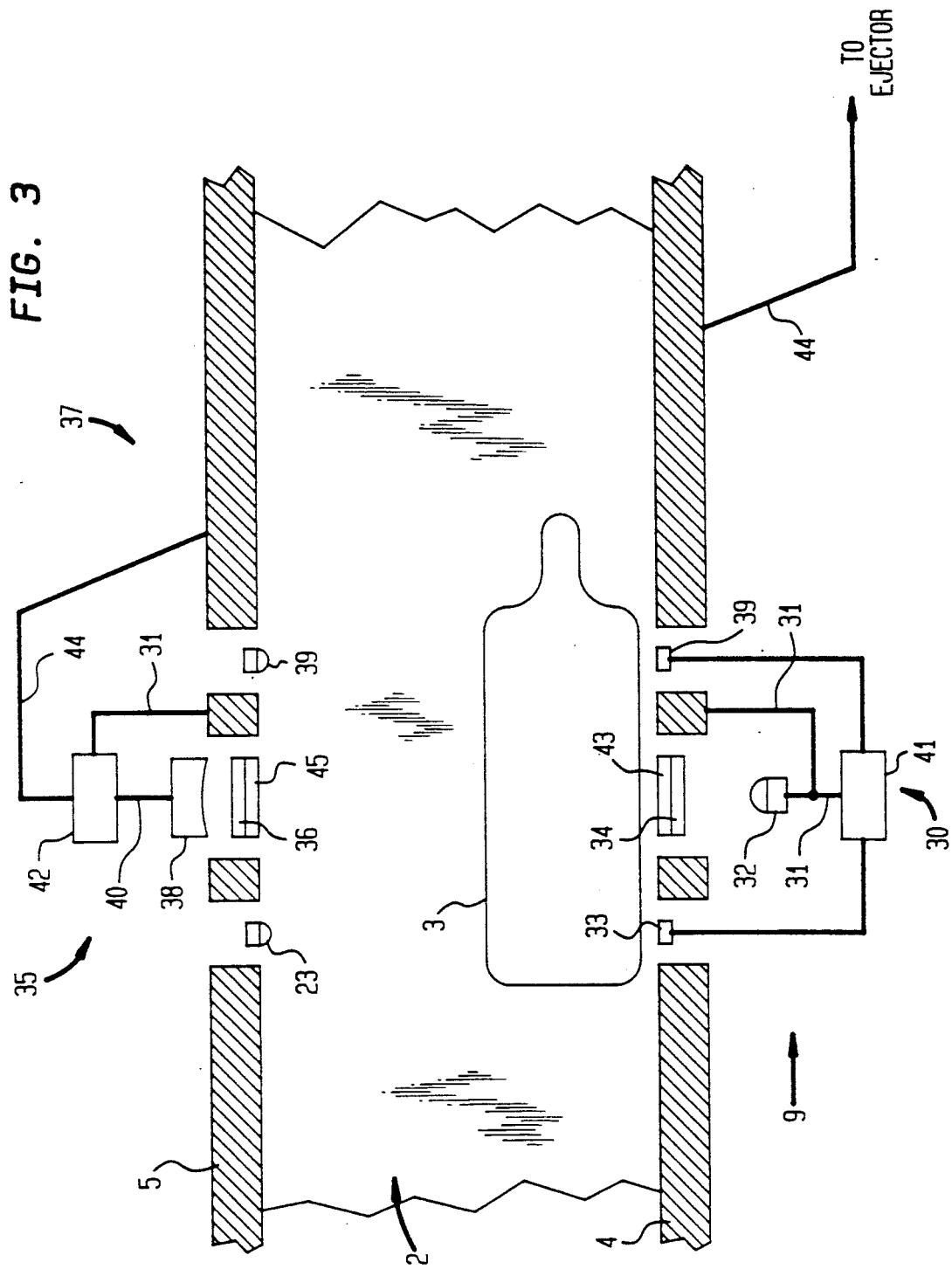
FIG. 3 is a plan view of the polarization sensing area.

Downstream and immediately adjacent X-ray sensing area 13 is polarization sensing area 37, shown in detail in FIG. 3. Polarization sensing area 37 distinguishes between PVC or glass and non-PVC plastic bottles by using circularly polarized light, and includes presence detectors 33 and 39, polarized light detector 35, ejector 46, and chute 49.

Presence detectors 33 and 39 are disposed on either side of emitter 30, so that presence detector 33 is upstream of the emitter and presence detector 39 is downstream of the emitter. Presence detector 33 includes an LED positioned on wall 5 and a photocell positioned directly across from the LED on wall 4. A beam of light is continuously emitted from the LED towards the photocell. Likewise, presence detector 39 also includes an LED on wall 4 and a photocell on wall 5, with a beam of light continuously emitted from this LED towards that photocell. The wavelength of the light used by presence detectors 33 and 39 is green, between 580–640 nm. The outputs of both of the photocells are fed into logic circuit 41. Logic circuit 41 outputs a predetermined signal when both of the light beams between presence detectors 33 and 39 are simultaneously attenuated. In turn, the output of logic circuit 41 is carried as an electrical signal on sample signal line 31 which is connected to polarized emitter 30. Thus, an electrical signal on sample line 31 will indicate that a bottle is presently disposed on the conveyor in front of emitter 30.

Polarized light emitter 30 is located in wall 4, and is connected to sample signal line 31. It is composed of light source 32, and polarizing filter 34. Light source 32 emits light for as long as it receives the predetermined signal from logic circuit 41 on sample signal line 31. Otherwise, no light is emitted by the light source.

Attached to light source 32 is polarizing filter 34 which linearly polarizes the light leaving the light source. Light leaving light source 32 is directed towards wall 5 and perpendicular to the direction of the conveyor. A quarter wave plate 43 is attached to the side of the linear polarizing filter 34 which is opposite light source 32. The quarter wave plate is made of a birefringent material whose thickness delays, for example, either the vertical or the horizontal component of the light by one quarter wave length with respect to the other. The quarter wave plate 43 is rotationally oriented with respect to the linear polarizer 34 so that the phase lead and phase lag directions of the quarter wave plate are 45° from the polarization direction of linear polarizer 34. Thus, circular polarized light is produced.

On the other side of conveyor 2 and directly across from emitter 30 is polarized light detector 35, which includes a quarter wave plate 45, polarizing filter 36, photocell 38, and output line 40. Detector 35 is positioned within wall 5, and receives the light emitted by the polarized light emitter 30. Quarter wave plate 45 is attached to polarizing filter 36 such that the polarizing filter 36 is between the quarter wave plate and photocell 38. Polarizer 36 and quarter wave plate 43 are oriented to filter out either the left or right handed circularly polarized light produced by filter 34 and quarter wave plate 43. Thus, if the quarter wave plate 43 slow direction is 45° clockwise from the polarization direction of filter 36, then quarter wave plate 45 should be oriented 45° clockwise with respect to the polarizing direction of filter 36. Once the quarter wave plate is in a fixed position with respect to the linear filter, the physical orientation of the circularly polarized filters at the emitter and detector does not matter.

The light leaving light source 32 which passes through polarizing filter 34, quarter wave plate 43, bottle 3, quarter wave plate 45, polarizing filter 36, respectively, is received at photocell 38, which passes the magnitude of the received light as an electrical signal on line 40. Thus, the magnitude of the electrical signal on line 40 is directly proportional to the magnitude of the light reaching photocell 38 from light source 32. Output line 40 is fed into a logic circuit 42. This logic circuit impresses either a high or very low current on output line 44, depending on whether the magnitude of the signal present on line 40 exceeds a certain threshold preset into the logic circuit. The output line 44 extends below conveyor 2, and is connected to ejector 46 (FIG. 1). The output of logic circuit 41 is also connected to the logic circuit 42, such that a signal will be impressed on line 44 only if bottle 3 triggers both presence detectors.

Ejector 46 is disposed on wall 4 and is downstream of polarized light emitter 30. The structure of ejector 46 is similar to the structure of ejector 23, as discussed above. On the other side of the conveyor and directly opposite ejector 46 is chute 49. Chute 49 leads to a storage bin (not shown) for all bottles diverted by ejector 46 (FIG. 1).

Figure 4:
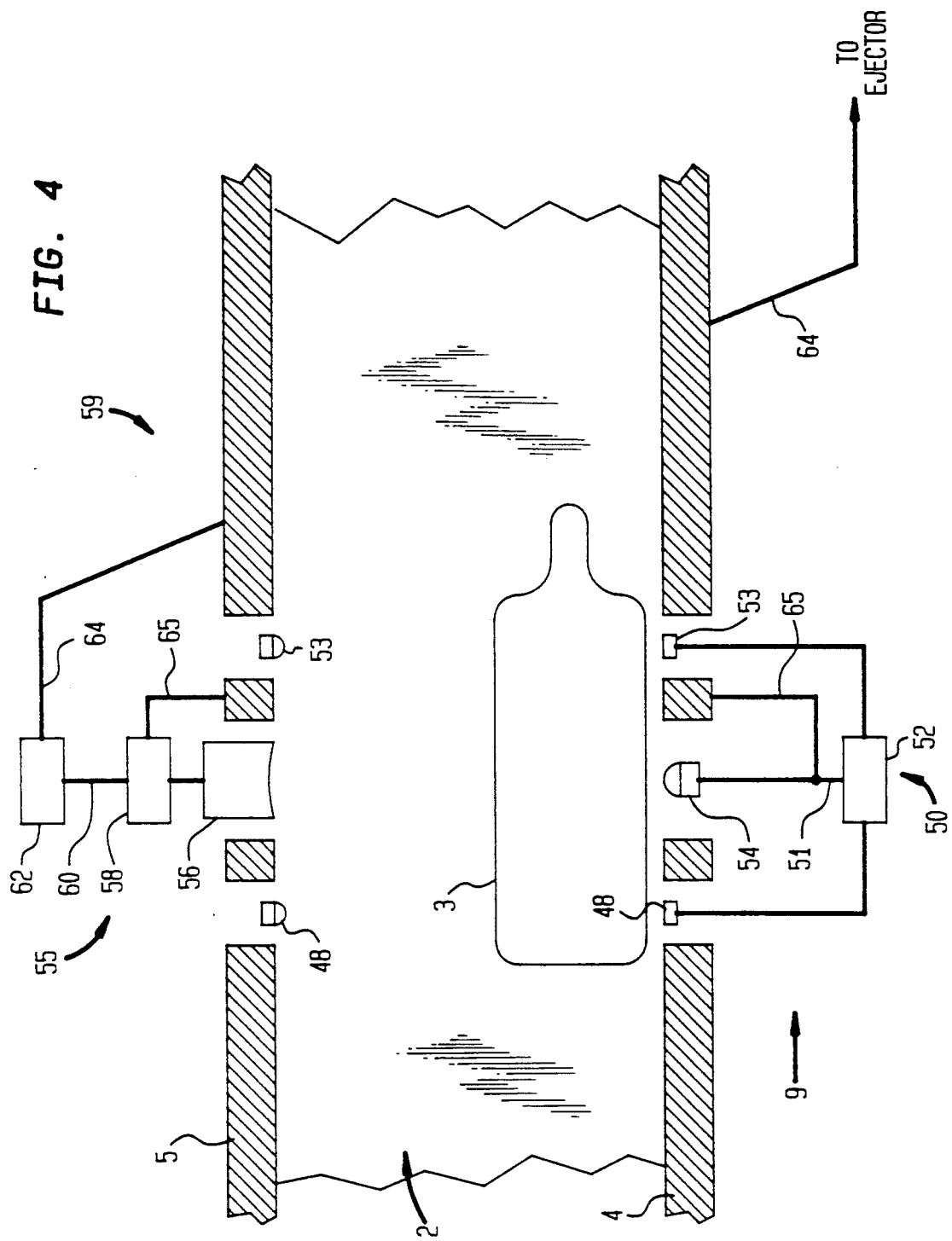
FIG. 4 is a plan view of the clear bottle sensing area.

Adjacent to and downstream from polarization sensing area 37 is the clear bottle sensing area 59, shown in detail in FIG. 4. Presence detectors 48 and 53 are located on either side of the emitter 50 and detector 55, and are used to impress a sample signal on line 51. The structure and operation of presence detectors 48 and 53 are essentially the same as discussed above for presence detectors 33 and 39, respectively. Emitter 50 is turned on when both beams of presence detectors 48 and 53 are simultaneously attenuated.

LED emitter 50 is positioned along wall 4 and includes sample signal line 51, modulator 52, and LED 54. LED 54 is turned on and off by modulator 52, which is in turn instructed to operate by the presence of an appropriate electrical signal along sample line 51. Modulator 52 modulates LED 54 such that the LED is turned on and off approximately 10,000 times per second. LED 54 transmits light preferably in the red light range (640–660 nm).

Red light detector 55 is positioned along wall 5 directly opposite from emitter 50. Detector 55 includes a photocell 56, demodulator 58, and logic circuit 62. Photocell 56 is located on wall 5 so that it may receive light coming from LED 54. The magnitude of the light received by photocell 56 is outputted to demodulator 58. Demodulator 58 is in communication with modulator 52 via wire 65, so that the demodulator is operated in synchronism with modulator 52. The output of the demodulator is carried on output line 60, and is in turn fed into logic circuit 62. Depending upon the signal from line 60, logic circuit 62 will impress either a high or low current on line 64. Sample signal line 51 is also connected logic circuit 62, such that a signal will be impressed on line 64 only if a bottle is present. Line 64 extends below conveyor 2, and is connected to ejector 61 located on wall 4. Ejector 61 operates in the same manner as previously discussed ejector 23. On wall 5 and directly across from ejector 61 is chute 69 for receiving clear bottles.

Downstream of clear bottle sensing area 59 is green bottle sensing area 73. The components of the green emitter 70 are the same as the components of clear emitter 50, namely, presence detectors, a modulator, an LED, a photocell, a demodulator, a logic circuit, and an ejector. Presence detectors 72 have the same structure and operation as presence detectors 33 and 39. Green emitter 70 is located on wall 4, and includes a modulator and an LED. However, the LED of green emitter 70 transmits only green light. The green light from emitter 70 will travel directly across the conveyor to green detector 75.

Green detector 75 includes the same components as clear detector 55. The modulator and demodulator of green emitter 70 and green detector 75, respectively, are modulated in synchronism via a common wire. Output line 76 carries an electric current whose value is either high or low, depending upon the output of the logic circuit within green detector 75.

Output line 76 is connected to ejector 78, which has the same structure and operation as ejector 23. If the value of the current along wire 76 is high, ejector 78 is activated and a high pressure blast of air is emitted in a direction towards chute 79. Chute 79 is across conveyor 2 and opposite ejector 78, and leads to a storage area (not shown) for all bottles diverted by ejector 78.

The next and last sensing area of the conveyor is translucent bottle sensing area 82. Translucent bottle sensing area 82 has similar components and operation as clear bottle sensing area 59 and green bottle sensing area 73. Emitter 80 emits high intensity red light, which can be sensed by detector 85. Ejector 88 is activated depending upon signals received from detector 85. Chute 89 receives any bottles directed by ejector 88. Emitter 80 can also be an infrared LED, for example, 930 mm.

After translucent bottle sensing area 82, conveyor 2 ends at terminal end 8. Attached to terminal end 8 is a chute 90 which leads to a storage area (not shown). Thus, bottles which have not been diverted by ejectors 23, 46, 61, 78 or 88 (i.e., opaque bottles) will fall off the conveyor, and enter chute 90.

In operation, bottles to be recycled, such as bottles 3, enter the conveyor from the feed mechanism 200. Walls 4 and 5 prevent the bottles from falling off the sides, and the sideways incline of the conveyor guides the bottles towards wall 4. As the conveyor 2 travels in direction 9, the bottles will first pass through X-ray sensing area 13. In this particular embodiment, X-ray unit emitter 10 and detector 20 are always on, and, therefore, X-ray emitter 10 will emit 6 KEV X-rays (shown as arrow 16) which will irradiate the bottle. If any chlorine is present within the bottle, such as would be the case if the bottle is composed of polyvinyl chloride (PVC) or polyvinylidine chloride (PVDC), the chlorine will fluoresce at 2.8 KEV under the parameters given above, and produce distinctive secondary radiation (shown as arrow 18).

The detector 20 will detect the presence of this signal. The detector 20 takes 200 samples a second, and the presence of 2.8 KEV secondary radiation is searched for each time. In fact, the sampling rate of the detector should be fast enough with respect to the speed of the conveyor so that at least 40-50 samples are taken per bottle. If any of the measurements detect chlorine, X-ray detector 20 will cause the current in wire 22 to go high, thus activating the solenoid control valve 24 of the ejector 23. Consequently, pressure will be diverted from pressure source 26 to blow out tube 28, and a stream of air will travel from the blow out tube towards the exit chute 29. The continuous movement of the conveyor 2 causes bottle 3 to enter this air stream, and the bottle is diverted into chute 29. The diverted bottle will travel down the chute until it reaches a storage bin specifically set aside for bottles containing chlorine.

If no chlorine is detected, no air stream will be created, and the bottle will proceed from X-ray sensing area 13.

The unit is extremely efficient in sensing the presence of chlorine. X-ray fluorescence occurs when a valence electron falls into the vacancy left by a core electron knocked out by a photon from the radiation source. A new photon is emitted with energy equal to the difference between the core and valence energy, which is always less than that of the original photon. Scattering may occur when a sample is irradiated, but in this case, incident photons are reflected with little or no energy loss. Thus, fluorescence can be readily distinguished from scattering. For example, the spectrum of an organic sample containing chlorine shows two broad peaks: an emission at 2.8 KEV resulting from florescence and a signal at 6 KEV resulting from scattering. Since chlorine fluoresces strongly at this energy, and because polyvinyl chloride (PVC) and polyvinylidine chloride (PVDC) bottles contain approximately 30% chlorine, the intensity of the peak at 2.8 KEV is roughly 10 times stronger than that at 6 KEV for PVC and PVDC plastic bottles. By contrast, in an organic sample without chlorine, the emission near 2.8 KEV, due largely to atmospheric argon, is ten times weaker than the scattered radiation at 6 KEV. This is a consequence of the fact that the light elements carbon, hydrogen, and oxygen scatter radiation efficiently but do not produce intense fluorescence near 2.8 KEV. The PVC detector is calibrated to correct for the effect of atmospheric argon on the readings.

Given the conditions under which the X-ray detector is used, the best results of detection are obtained when a bottle is no more than one-half inch away from X-ray detector 20, because fluorescent intensity falls more quickly over distance than does back-scattered and argon fluorescence intensity. Dirt does not seem to greatly reduce the sensitivity, but X-ray detector 20 cannot detect through the paper labels which are routinely attached to the bottle 3. Consequently, if X-ray detector 20 takes approximately 40-50 samples per bottle, then approximately 12 to 20 samples will be made to those portions of a bottle not covered by a label. The X-ray detector 20 could be set to detect only chlorine levels above a certain threshold. In the preferred embodiment, however, a very low threshold is used, and the presence of any chlorine will activate the ejection signal.

Ideally, each sample bottle should have a fixed fluorescence count. In reality, the counts from a single sample are expected to vary slightly from one measurement to another. Assuming the readings follow a normal statistical distribution, the standard deviation around a given peak can be equated to the square root of a mean reading, and such standard deviations (or "sigmas") may be used as a measure of the suitability of fluorescence detection for distinguishing between those bottles containing chlorine and those bottles which do not. For example, a difference of 5 sigmas between 2 samples, such as would exist between one with a mean fluorescence count of 10,000 and one with a mean count of 9,500, would indicate that mistakes in discriminating between the two bottles would occur only 6 times per million bottles. At 600 bottles per minute, an error should occur only once every 50 hours. In fact, since several determination loops are run in a bottle over the time that it passes the fluorescence head, the error rate for missing a PVC bottle is even lower.

When a bottle 3 leaves X-ray sensing area 13 and enters polarization sensing area 37, as shown in FIG. 3, the light beams generated between presence detector 33 and 39 are interrupted. If both beams of light are simultaneously broken by the presence of a bottle between the LEDs and photocells, the logic circuit 41 impresses an appropriate electrical signal on sample signal 31. Thus, polarized light emitter 30 is instructed to operate.

During operation of light emitter 30, light source 32 will be on and light will be directed from the light source on wall 4 towards detector 35 on wall 5. As the light leaves light source 32, it passes through polarization filter 34 and quarter wave plate 43, thus creating a beam of circularly polarized light.

Before the polarized light reaches detector 35, it passes through bottle 3 and its polarization is changed to a degree dependant upon the composition of bottle 3. For example, if the bottle is PET, the polarized light passing through the bottle will change rather substantially. If the bottle is PVC or glass, the polarization of the light will not be affected nearly as substantially. In other words, since the combination of quarter wave plate 45 and linear polarizer 36 will not pass any light of the polarized light produced by passage through filter 34 and quarter wave plate 43, if a signal is received at detector 38, the bottle must have altered the polarization of the light.

In other words, as the change in polarization increases, the amount of light reaching photocell 38 also increases. Therefore, if the light reaching the photocell 38 is more than a certain threshold value, then substantial polarization change occurred and bottle 3 must not be PVC or glass, and is probably PET. On the other hand, if the amount of light reaching photocell 38 is below that threshold, then the material must be glass or a plastic containing PVC.

Therefore, if bottle 3 is PET, the signal along line 40 will be high, logic circuit 42 will impress a low current on output line 44, and ejector 46 will not be activated. If bottle 3 is glass or PVC, the signal carried on output line 40 will be low, logic circuit 42 will impress a high current on output line 44, and ejector 46 will create an air jet in the direction of chute 49. If a bottle is moved into this air stream, it will be diverted into chute 49, and conveyed to a storage bin (not shown) for glass and PVC bottles. The point at which logic circuit 42 will impress a low or high current may be varied. Thus, an operator or technician may adjust the threshold level to correspond with the glass and plastic that typically passes through the recycling system.

Thus, polarization sensing area 37 will divert two different categories of bottles: glass and PVC. Polarization sensing area 37 may serve as either a supplement to the X-ray sensing area 13, or stand on its own. If the X-ray sensing area is upstream of polarization sensing 37, the X-ray sensing area will remove the bottles containing chlorine, leaving the polarization sensing area to remove the glass bottles from the remaining bottle stream. Alternatively, if X-ray sensing area 13 is omitted, polarization sensing area 37 will remove the PVC bottles along with glass bottles from the bottle stream. Although it is not shown, instead of sending the glass and PVC bottles to the same storage bin, the diverted bottles could be passed through another polarization sensing area similar to polarization sensing area 37. While non-PVC plastic bottles greatly change polarized light in comparison to PVC and glass bottles, PVC bottles do change polarized light slightly more than glass bottles. In a mixture of glass and PVC bottles, this second polarization area would detect this difference between glass and PVC. The glass and PVC bottles would be sent to separate streams, each destined for their own storage bin. The two polarization areas could also be used in series. Since non-PVC plastic bottles affect polarized light the most, glass the least, and PVC bottles somewhere in between, the first polarization area could have a threshold adjusted to remove only glass bottles, and the second polarization area could have a threshold adjusted to remove all PVC bottles. The remaining bottles would be non-PVC plastic bottles, and would continue down the conveyor.

Along with PVC bottles, PVDC bottles will also be diverted, as the principles discussed above with respect to PVC bottles are equally applicable to PVDC bottles.

In the polarization sensing area 37, it also preferable to use two light sources, each of opposite polarization, to account for problems caused by high-optical density. For example, if an opaque or optically dense bottle is present, all the light leaving light source 32 will be blocked completely, giving a false signal of PVC or glass regardless of the bottle's composition. By adding a second light source (not shown) polarized to give photocell 38 the most light with no rotation, the problems caused by optically-dense bottles can be avoided. The second polarized light source has the opposite polarization of the first. The two sources would be modulated, so emitter 30 would be off while the second emitter is on, and emitter 30 would be on while the second is off. Logic circuit 42 would be operated in sync with the light sources, such that it is aware of which light source is presently on. If the bottle is PVC or glass, the light beam from light source 32 will be relatively unrotated and little light will reach photocell 38, while most of the light from the second light source will reach photocell 38. On the other hand, if the bottle is non-PVC, the light beam from light source 32 will be rotated and most of the light beam will reach photocell 38, while little of the light from the second light source will reach the photocell. If the bottle is opaque, neither light beam from either light source will reach photocell 38, and logic circuit 42 would recognize the condition and pass the bottle onto the optical sensors. As a practical matter, the light sources should be as close to each other as possible, so that local variations in the bottle such as dirt, thickness, and bottle curvature will affect each beam the same. Preferably, the light beams would be substantially coaxial.

While the basic principles also apply to linear polarization, circular polarization provides unique advantages. If linear polarization filters are used, the filters must be mechanically stable such that the orientation of the filters at the emitter remains constant with respect to the detector. Linear filters are physically vertically and horizontally oriented, so that light passing through a vertically oriented filter will be completely blocked by a horizontally oriented filter, but will pass unattenuated through a vertically oriented filter. A horizontally linear filter could become a vertically linear filter merely by physically rotating the filter 90 degrees. Because any recycling system would be subject to jarring by the operators and bottles, the physical rotation of the linear filters would have to be periodically checked to test their alignment. Circular polarization does not require proper physical alignment. Right-handed circular polarization filters will block left-handed circular polarized light no matter what the physical angle of the filter.

Another advantage of circular polarization over linear polarization is that the orientation of the bottle itself becomes less important. It is possible that a highly birefringent bottle would have an "angle of rotation" coincidentally matching the angle of rotation of the linearly-polarized light beam, merely due to the angle of the bottle with respect to the light beam. If so, the light would pass through the bottle relatively unchanged, giving a false signal of nonbirefringent bottle. A circularly polarized light beam avoids this possibility because the wave vector goes through all angles and directions, and will be affected by the birefringence of the bottle no matter what the bottle's orientation.

After a bottle 3 passes through polarization sensing area 37, it enters clear bottle sensing area 59 shown in detail in FIG. 4. As the bottle enters this area, it attenuates the light beams emitted between presence detectors 48 and 53. The simultaneous attenuation of these beams causes a sample signal to be impressed on sample signal line 51, which in turn causes modulator 52 to turn LED 54 on and off at the predetermined modulated frequency. The light emitted by LED 54 travels across conveyor 2, through bottle 3, and to photocell 56. The magnitude of the light received by the photocell is outputted to demodulator 58.

Modulator 52 and demodulator 58 are operated together to diminish the effect of ambient light. When LED 54 is off, the magnitude of the light detected by photocell 56 will correspond with the amount of ambient light. When LED 54 is on, the magnitude of the light detected by photocell 56 will be equal to the amount of ambient light reaching photocell 56 in addition to the light received from LED 54. Thus, demodulator 58 outputs the magnitude of the difference, i.e., the amount of light directly attributable to LED 54. The current on line 60 is proportional to the magnitude of the light received by photocell 56 from LED 54.

Since LED 54 emits red light, the amount of light reaching photocell 56 will be approximately equal to the amount of light leaving LED 54 if the bottle is clear. Thus, if bottle 3 is clear, substantially all of the light leaving LED 54 will reach photocell 56, and the current carried on output line 60 will be high. Further, if the current on line 60 is higher than a certain threshold already set within logic circuit 62, logic circuit 62 will impress a high current on line 64. On the other hand, if bottle 3 is not clear, then the light leaving LED 54 will be attenuated by the bottle before it reaches photocell 56, and the electric current carried on output line 60 will be lower. If the current on line 60 is lower than the set threshold, then logic circuit 62 will impress a very low current on line 64. This threshold can be varied by technicians and operators of the recycling sorting system to vary with needs of the system.

Ejector 61 will be activated only if the current on line 64 is high, i.e., if the light passing through the bottle was not significantly attenuated. If ejector 61 is activated, then bottle 3 will enter the subsequent air stream and be diverted to chute 69. Once in chute 69, the bottle will travel down the chute until it reaches a storage bin for clear bottles (not shown). Most of the bottles diverted to chute 69 will be clear PET (polyethylene therephtalate) bottles. Otherwise, if bottle 3 is not clear, ejector 61 will not be activated and the bottle will pass to the next sensing area, green bottle sensing area 73.

The operation of green bottle sensing area 73 is essentially the same as clear bottle sensing area 59. As the bottle enters this area, it interrupts the light beams emitted between presence detectors 72. The interruption of these beams causes a sample signal to be impressed on signal line 71, which in turn causes a modulator to turn green LED on and off at the predetermined frequency. The light emitted by green light emitter 70 travels through bottle 3, across conveyor 2, and towards green light detector 75. Since emitter 70 emits green light, a substantial amount of this light will reach detector 75 if bottle 3 is green. On the other hand, if the bottle is not green, most of the green light will be attenuated, and detector 75 will not receive as much green light as it would for a green bottle.

The light reaching green light detector 75 is demodulated, and the signal from the demodulator is fed into a logic circuit. If the light was relatively unattenuated, such as would be the case if the bottle was green, the logic circuit will impress a high current on output line 76. If the light was significantly attenuated, then the logic circuit will impress a low current on output line 76.

Ejector 78 will be activated if the current output line 76 is high, and bottle 3 will enter the subsequent air steam and be diverted to chute 79. Bottle 3 will travel down the chute until it reaches a storage bin for green bottles (not shown). Most of the bottles diverted into chute 79 will be green PET bottles. If bottle 3 is not green, ejector 78 will not be activated, and the bottle will pass to the next sensing area, translucent bottle sensing area 73.

The operation of translucent bottle sensing area 82 is essentially the same as green bottle sensing area 59. As the bottle enters this area, it simultaneously interrupts the light beams emitted between presence detectors 83. The interruption of these beams causes a sample signal to be impressed on sample signal line 81, which in turn causes a modulator to turn a high intensity red I&ED on and off at a modulated frequency. The light emitted by high intensity red light emitter 80 travels through bottle 3, across conveyor 2, and towards light detector 85.

Since emitter 80 emits high intensity red light and most transparent bottles have been removed, the amount of light reaching detector 85 will distinguish between translucent and opaque. In other words, if the bottle is nearly opaque, very little light will reach detector 85. If the bottle is translucent, sufficient light to trigger bottle ejection will reach detector 85.

The light reaching light detector 85 is demodulated and an electrical signal proportional to the amount of light reaching detector 85 from emitter 80 is created and inputted into a logic circuit. The logic circuit will impress a high current on line 86 if the electric signal exceeds a predetermined threshold, and a very low current on line 86 if the electrical signal is below that threshold. Ejector 88 will activate if the current on wire 86 is high, thus signalling the presence of translucent bottles. Ejector 88 will be activated, and bottle 3 will enter the subsequent air stream and be diverted to chute 89. The bottle will travel down the chute until it reaches a storage bin for translucent bottles (not shown). Most of the bottles diverted into chute 89 will be translucent high-density polyethylene (HDPE) bottles. Otherwise, if the bottle is not translucent, ejector 88 will not be activated and the bottle will pass to the end of the conveyor 8.

Disposed at the end of the conveyor 8 is a chute. If a bottle has passed all of the previous sensing areas, then it has significantly attenuated all the light leaving the various light sources, and must be opaque. The bottle will travel down the chute until it reaches a storage bin (not shown) for opaque bottles. Most of the bottles which reach the chute will be opaque HDPE bottles.

The order of sortation promotes a highly accurate and cost-efficient sortation method. Initially, PVC, PVDC and glass bottles are removed. After these have been preliminarily removed, the first bottles removed are clear. Next, green bottles are removed after the clear bottles. If the clear bottles were not removed beforehand, the green bottle sensor would eject a mix of green and clear bottles, rather than only green bottles. Also, if a clear bottle was mistakenly missed by the clear bottle sensor, it will be removed along with the green bottles because green light will pass through the bottle relatively unattenuated. If a few clear bottles are shredded along with green bottles, the market value of the shredded green mix will not be decreased because the green color of the mix will be relatively unaffected by a few clear bottles. The converse of this is not true. A few green bottles within a shredded clear bottle mix will adversely affect the quality and value of the mix. Bottles which have passed all the sensors are diverted to a storage bin for opaque bottles. At this point, it is highly likely that any clear and green bottles would have been removed in the translucent sensing area. A few translucent bottles among opaque bottles will not affect the value of the opaque HDPE bottle mix.

Figure 5:
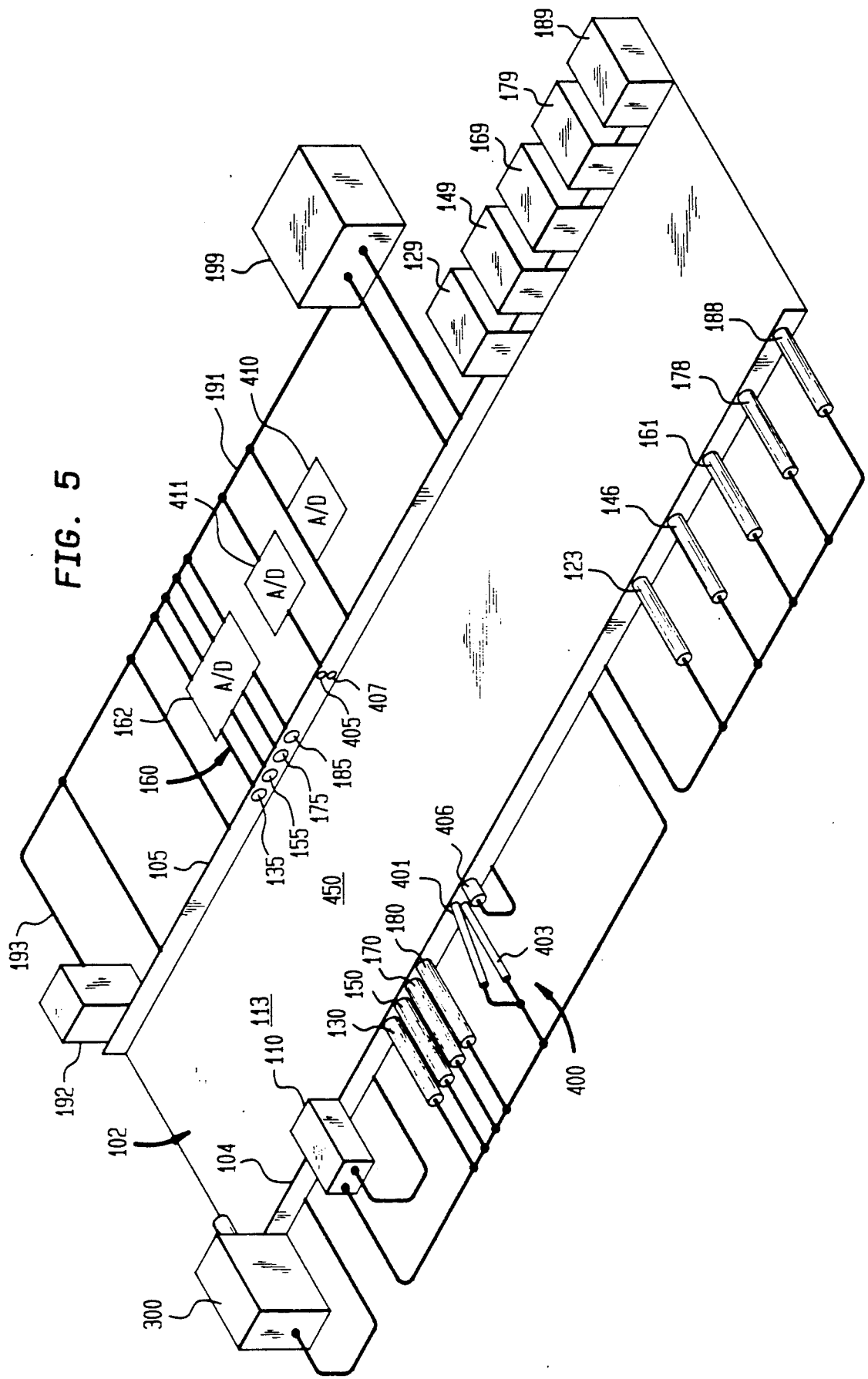
FIG. 5 is a perspective of another of the preferred embodiments of the present invention.

Another preferred embodiment of the present invention is illustrated in FIG. 5. This embodiment differs from the multi-station system of FIG. 1 in that the outputs of the various sensing areas are fed into a computer, which diverts the bottles by considering and comparing all the different outputs. This embodiment may be referred to as a single station system, since the ejectors are not necessarily activated by the output of a single sensor, but instead may be activated dependant upon particular combinations of many sensors.

Essentially, the components and operation of the individual emitters and detectors are the same. For example, X-ray detection unit 110 of X-ray sensing area 113 has the same components and operation as X-ray emitter 10 and detector 20 of X-ray sensing area 13; polarized light emitter 130 and detector 135 of polarization sensing area 137 have the same components and operation as emitter 30 and detector 35 of polarization sensing area 37; red light emitter 150 and detector 155 of clear bottle sensing area 159 have the same components and operation as emitter 50 and detector 55 of clear bottle sensing area 59; green light emitter 170 and detector 175 of green bottle sensing area 173 have the same components and operation as emitter 70 and detector 75 of clear bottle sensing area 73.

There are a few differences between the preferred embodiment of FIG. 1 and the preferred embodiment of FIG. 5. First, the output lines of the various detectors are fed into analog-to-digital converters instead of logic circuits, and the converted output signals are then routed to a central computer 199 via bus 191. Output wires 160 from the polarizing, red, green, and high-density red detectors 135, 155, 175 and 185, respectively, are fed into an analog-to-digital converter 162, with the digitized signals fed into bus 191.

A second difference is that the chutes are positioned at the end of the conveyor. Instead of a disposing a chute after each detector, a bottle will pass all the sensing areas before arriving at chutes 129, 149, 169, 179, 189, all of which are arranged along wall 105. The ejectors associated with these chutes are 123, 146, 161, 178 and 188, respectively, and are disposed along wall 104, directly opposite their respective chutes.

A third difference is the addition of conveyor speed detector 192. Speed detector 192 detects the speed of the conveyor and outputs this information as a digital signal on wire 193, which is connected to bus 191. Because many bottles may be on conveyor 102 at the same time, computer 199 may receive information from many sensors simultaneously. Therefore, computer 199 tracks the position of any individual bottle and its associated sensing results by tracking the speed of the conveyor. By operating in this manner, computer 199 can compile information on multiple bottles simultaneously, resulting in a high-speed sortation method.

A fourth difference is the movement of the polarizing, red, green, and high intensity or infrared red LEDs to the same sensing area. Because the single-station system as shown in FIG. 5 does not have an ejection system after each sensor like the multi-station system of FIG. 1, the optical sensors need not be far apart. Thus, as shown in FIG. 5, the optical sensors are relatively close to one another. In fact, it is advantageous to put the light emitters and detectors as close to one another as practical, so readings will be made from the same local area of the bottle. The general area between emitters 130, 150, 170 and 180 and detectors 135, 155, 175 and 185 is referred to as optical sensing area 450.

A fifth difference is the removal of the presence detectors described beforehand, and the addition of a bottle length detector 400. The bottle length detector 400 serves two functions: To measure the length of the bottle and to trigger the set of optical emitters 130, 150, 170 and 180 and their associated detectors. The bottle length detector 400 should be no greater than one bottle length away from the optical emitters 130, 150, 170 and 180. Bottle length detector 400 comprises two light beams, one of which is preferably circularly polarized and the other a color, such as red. Specifically, red LED 403 on wall 104 directs a red light beam across conveyor 102 towards concave mirror 405 on wall 105, which reflects the light beam into photocell 406 on wall 104. The beam is on continuously. The magnitude of the light reaching photocell 406 is digitized by analog-to-digital converter 410, and sent to computer 199 via bus 191. Simultaneously, polarization emitter 401 emits a circularly polarized light beam downward and across conveyor 102 towards polarization detector 407. As discussed previously with respect to the polarization sensing area 137, the magnitude of the circularly polarized light received by the detector 407 is digitized by analog-to-digital converter 411 and sent to computer 199 via bus 191. The polarized light beam is directed at an angle with respect to the plane of conveyor 102 so it is not coaxial with the red light beam, and, therefore, both beams will cover different areas of any bottle in the area. The use of a polarized light beam prevents the possibility that a very clear bottle will go undetected by the red light beam, and the red light beam prevents the possibility that a nonbirefringent bottle will go undetected by the polarized light beam. The addition of other light beams with different characteristics would also increase the accuracy of the bottle length detector.

If computer 199 recognizes that one of the light beams from bottle detector 400 has been attenuated, then a bottle must be present in the area. Since the bottle length detector 400 is close to the optical sensing area 450, it can be assumed that the bottle is also in the optical sensing area. Consequently, the computer will send a sample signal to the polarization, red, green and high intensity red emitters 130, 150, 170 and 180 to begin emitting light, and will begin reading the outputs from detectors 135, 155, 175 and 185. Thus, the bottle length detector also serves as a presence detector for optical sensing area 450. Simultaneously, the bottle counts the length of time from the first attenuation of the bottle detector light beams to the end of the attenuation. This will yield the length of the bottle, which is useful for a variety of reasons. First, the air jets could be activated only when the center of the bottles are adjacent to the jet, thus ensuring a reliable trajectory. Second, the bottle length itself may be useful in determining the category of the bottle, as will be explained further.

The operation of the preferred embodiment of FIG. 5 is similar to the operation of FIG. 1. A bottle 103 passes through X-ray sensing area 113, and its chlorine content is analyzed. However, unlike the embodiment of FIG. 1, the bottle is not immediately ejected if X-ray sensor 110 detects the presence of chlorine. Instead, the output of X-ray sensor 110 is sent to computer 199 via bus 191, and stored in the memory of the computer. Bottle 103 then proceeds to optical-sensing area 450. As a portion of the bottle exits the optical-sensing area, it will attenuate one of the light beams of the bottle-length detector 400. The computer will then trigger emitters 130, 150, 170 and 180 to emit light, and will also read the outputs from the detectors 135, 155, 175 and 185. The output signals of the optical sensors are then stored in the memory of the computer. As the bottle passes out of optical-sensing area 450 and beyond bottle-length detector 400, the computer counts the time from the first attenuation to the last attenuation and thusly determines the length of the bottle. The computer will also instruct the emitters to cease emitting light, and will also cease reading the optical sensor outputs once the bottle leaves optical sensor area 450.

The computer 199 uses the outputs of the various sensors, including bottle length, to determine certain properties of the detected bottle. The attenuation of the individual light beams of the optical sensors may be used to determine a bottle's properties, such as if the bottle is green, clear or translucent. For example, if the attenuation of the green light beam is less than a certain threshold preset in the computer, then a bottle with a green property would be determined to be present. Alternatively, since the clear (red light beam), green (green light beam), and translucent (high intensity red light beam) signals are all fed into the computer, the outputs of the sensors can be compared to one another to determine the properties of the bottle. For example, instead of merely assuming a green bottle is present if the green light is relatively unattenuated, the attenuation of the green light may be compared to the attenuation of the red light. If the ratio of the magnitude of transmitted green light to the magnitude of transmitted red light is significantly greater than one, it may be determined quite assuredly that a green ."property" is present. Similarly, if the ratio of transmitted IR light to transmitted green light is significantly greater than one, then a translucent "property" is assumed present. However, if the ratios do not result in clear determinations, then the computer would realize that physical characteristics such as wrinkles, dirt, scratches, and bottle curvature prevent the bottle from being accurately characterized, and the bottle may be diverted to a bin for manual sorting. In any event, the outputs of the sensors are used to determine the properties of the bottle.

The combination of properties are then fed into a truth table, which determines the category of the bottle on the basis of its properties. The bottle is assigned to the category listed in the truth table that first matches the boolean variable values of the bottle.

the height of the bottle may add a bottle-height property.

The particular category of the bottle is outputted on bus 191, which sends a signal to one of the ejectors 123, 146, 161 or 178. The ejector associated with that category will be activated, and an airstream will be sent across conveyor 2 towards one the chutes 129, 149, 169 or 179. The bottle will enter the airstream, and then be diverted to the appropriate chute. Thus, each ejector and chute is associated with a desired category of bottle. For example, a bottle containing PVC or PVDC may be diverted by ejector 123 into chute 129, and travel to a storage bin for bottles containing chlorine.

Although the truth table above uses absolute values of true and false to determine the category of the bottle, it is also possible to assign ranges of values to the properties, and compare those ranges of values with stored ranges of values for known categories of bottles. For instance, the computer will compare the magnitude of the "greenness" of a particular bottle with a predetermined range of values associated with different types of green PET bottles. Further, because a particular level of green in a bottle may be associated with more than one bottle category (such as green HDPE bottle versus a green PET bottle), the outputs of the other sensing areas may also be compared and classified. The results from all the different comparisons would be fed into a more expansive predetermined truth table which would allow a particular combination of all the magnitudes of all the sensors to classify the bottle into one category.

It will be noted that the above truth table essentially reflects the order of sortation of the first embodiment shown in FIG. 1. For example, in the first embodiment, in order for a bottle to be directed into the green bottle chute, it must first pass through the clear bottle sensing area before being ejected in the green bottle sensing area. The truth table performs the same test. After passing through all the sensing areas, the bottle will be directed to a green bottle chute if the various outputs indicate that the bottle did attenuate red light, i.e., the bottle is not clear, and that this bottle did not attenuate green light, i.e., the bottle is green. A second similarity between the two preferred embodiments is the handling

| Bottle Category | Property | | | |
|---|---|---|---|---|
| | GREEN | TRANSLUCENT | OPAQUE | BOTTLE-LENGTH |
| Clear bottles | FALSE | FALSE | FALSE | NOT ZERO |
| Green bottles | TRUE | x | FALSE | NOT ZERO |
| Translucent bottles | FALSE | TRUE | x | NOT ZERO |
| Opaque bottles | x | x | TRUE | NOT ZERO | x = state is irrelevant to determination

Thus, a bottle whose property values of GREEN, TRANSLUCENT, OPAQUE, and BOTTLE LENGTH are, respectively, true, true, true and not zero, is assigned to the opaque bottle category. Similarly, a bottle with the property values of, respectively, false, false, false and not zero is assigned to the clear bottle category. Although not shown in a truth table, the presence of chlorine could also be used as a property to categorize the bottles. Further, other sensors may be used to add further properties in the discrimination of bottle category. For example, sensors directed to of misidentified bottles. In the first embodiment, if a clear bottle mistakenly passed through the clear bottle sensing area, it would still be diverted in the green bottle sensing area. The truth table uses the same property to the same advantage. Even if the clear bottle is not detected as a clear bottle, it will still pass green light relatively unattenuated, and be considered a "green" bottle. Therefore, according to the truth table, this clear bottle would be diverted to a green bottle holding bin. As discussed fully above, the marketability of the green bottle mix will not be adversely affected by the presence of a few clear bottles. Thus, both embodiments preserve the marketability and quality of the various sortation categories, even if a bottle is incorrectly identified.

An additional advantage of this method and apparatus is that it allows the system to determine whether a mistake has been made for a particular bottle. For example, if then an error has occurred. In such a case, the possible options include sending the bottle to the opaque bottle storage bin, the clear bottle storage bin, or a separate storage bin for bottles which produce contradictory sensing area outputs. The particular option desired will vary with the needs of the user.

In a preferred arrangement, the embodiment shown in FIG. 5 is provided with UPC detector 300 in addition to the other sensors discussed above. Most bottles sold at retail stores include a Universal Product Code (UPC) label, which is a printed binary code associated with one particular bottled product. The UPC code is specific to many levels of an individual catalog item, i.e., not only a specific product and brand, but also a specific container. Almost without exception, each such item is packaged in only one type of bottle. Thus, one bottle type is associated with each UPC code. If this association is known, the UPC can be used to determine the category of bottle passing by the UPC detector.

The operation of the UPC detector is similar to the operation of the other sensing areas. As a bottle 3 passes by UPC detector 300, which may be one known in the art, the detector scans the bottle for the existence of UPC label. If a readable UPC label is found, the code is transmitted to computer 199 via bus 198, and computer 199 will search its memory to determine if it has a record of that particular code. Any record of the code would include the type to which the bottle belongs. If a record exists for that code, the computer will output the particular category to the ejectors located at the end of the conveyor when the bottle arrives near the ejectors. As discussed above, the bottle will be diverted accordingly.

It can be expected that a valid UPC label will be more reliable than the other sensors of the recycling system. Therefore, if a valid UPC is scanned, the outputs from the sensors can be ignored, and the bottle will be diverted on the basis of its UPC alone. Alternatively, the outputs of the other sensors could be used to double check the accuracy of UPC detector 300. Bottles which create outputs contradictory to the UPC detector could be diverted to a separate bin, for later analysis or manual sorting.

In any event, since a large portion of bottles to be recycled do not have readable UPC labels by the time they reach a recycling center, an efficient recyclable bottle sorter usually cannot rest on the use of UPC detectors alone. Therefore, a UPC detector normally should be considered a complement to an efficient recycling system, and not a replacement.

Figure 6:
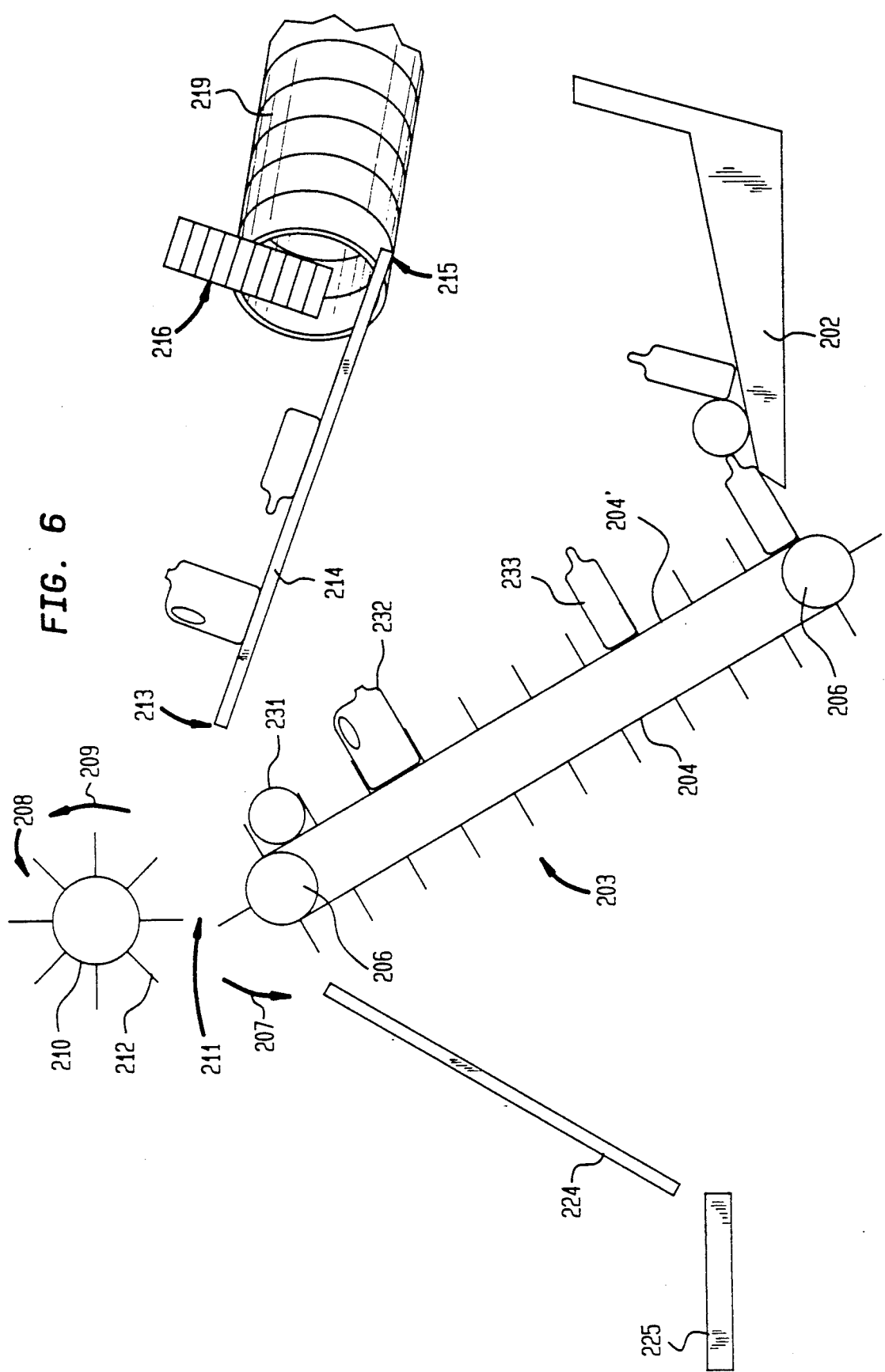
FIG. 6 is a perspective view of a bottle feed mechanism according to one embodiment of the present invention.
Figure 7:
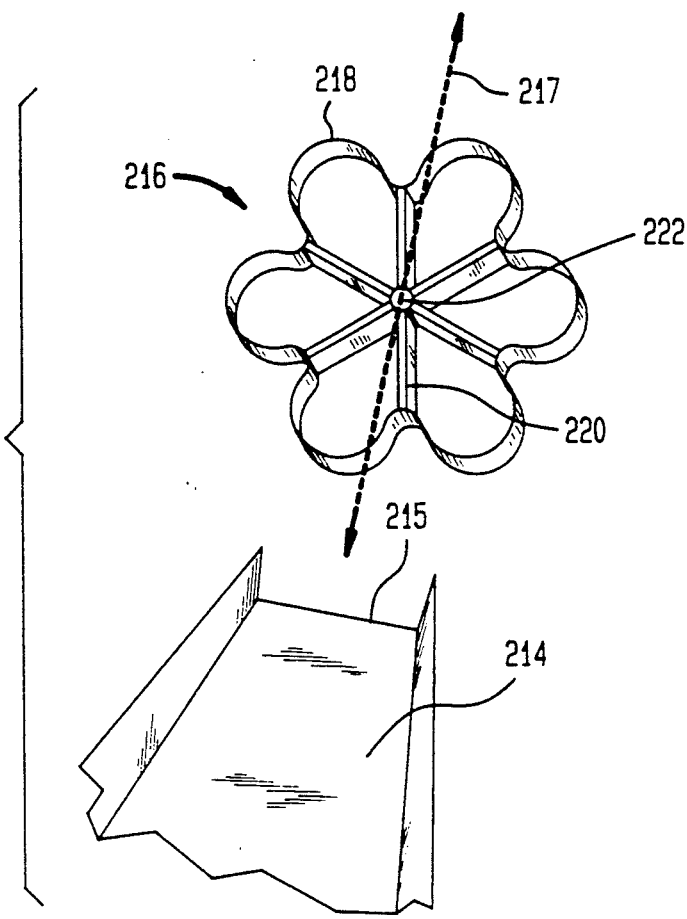
FIG. 7 is a perspective view of the second paddle wheel of the bottle feed mechanism.

A preferred embodiment of the feed mechanism for either embodiment is illustrated in FIGS. 6 and 7. As seen in FIG. 6, a bin 202 receives and holds bottles to be sorted for recycling. Bin 202 is slightly inclined, and positioned at the lowest end of the bin is inclined conveyor 203. Inclined conveyor 203 includes a continuous belt 204 having an upper run 204' which extends between pulleys 206. Pulleys 206 are rotated by motor means (not shown). Pulleys 206 revolve in a counterclockwise direction thereby advancing the upper run 204' towards the upper pulley 206a. Attached to the outer surface of belt 204 are cleats 205, which are spaced from one another and preferably inclined at a 90 degree angle to the outer surface of belt 204.

Disposed above the highest point of inclined conveyor 203 is first paddle wheel 208. Paddle wheel 208 rotates in the counter-clockwise direction 209. First paddle wheel 208 has a cylinder 210 with a plurality of paddles 212 extending radially outward from the outer surface of the cylinder. The length of paddles 212 are such that the outermost edges of the paddles remain a spaced distance from the closest point of conveyor belt 204, this distance being slightly greater than the diameter of the desired smaller bottles. Preferably, this distance is slightly greater than the diameter of a standard two-liter plastic bottle. The narrowest gap between the paddle wheel 208 and inclined conveyor 203 is indicated at 211.

Above almost the entire length of inclined conveyor 203 is slide 214, which is also inclined. The top edge 213 of the slide is near gap 211. Bottom edge 215, which is lower than top edge 213, is positioned above the bin 202. The upper surface of slide 214 is smooth, and encourages the easy sliding of bottles on its surface from top edge 213 to bottom edge 215.

Positioned above and near bottom edge 215 of slide 214 is second paddle wheel 216. As shown in FIG. 7, paddle wheel 216 includes a rotating shaft 222, spokes 220 radially extending from the shaft, and paddle belt 218 attached to the ends of the spokes. Because shaft 222 is rotated by a motor (not shown), paddle belt 218 rotates about an axis of rotation 207 extending longitudinally through shaft 222. The outer surface of paddle belt 218 alternatively extends closer to and farther away from axis of rotation 217. Thus, certain portions of paddle belt 218 extend beyond other portions of the paddle belt, and effectively form paddles. Slide 214 is tapered towards bottom edge 215, such that top edge 213 is wider than bottom edge 215. Walls on either side of the slide cause objects travelling down the tapered slide to move towards the center, thus forcing objects to slide directly under paddle wheel 216. Second paddle wheel 216 is positioned above bottom edge 215 such that a spaced distance always remains between slide 214 and the outermost points on the second paddle wheel. Preferably, this distance is slightly greater than the diameter of standard two-liter plastic bottles. As seen in FIG. 6, the axis of rotation 207 is substantially parallel to the plane of the upper surface of slide 214, and parallel to the upstream-to-downstream axis of the slide 214. Thus, upon rotation about this axis, the periphery of the wheel moves in a direction orthogonal to the upstream-to-downstream extent of the slide end orthogonal to the path of an object sliding down slide 214 from top edge 213 to bottom edge 215.

A chute 219 is positioned adjacent paddle wheel 216 and the bottom edge 215 of slide 214. Chute 219 will receive any bottles diverted by second paddle wheel 216, and leads to a storage bin for oversized bottles.

Figure 8:
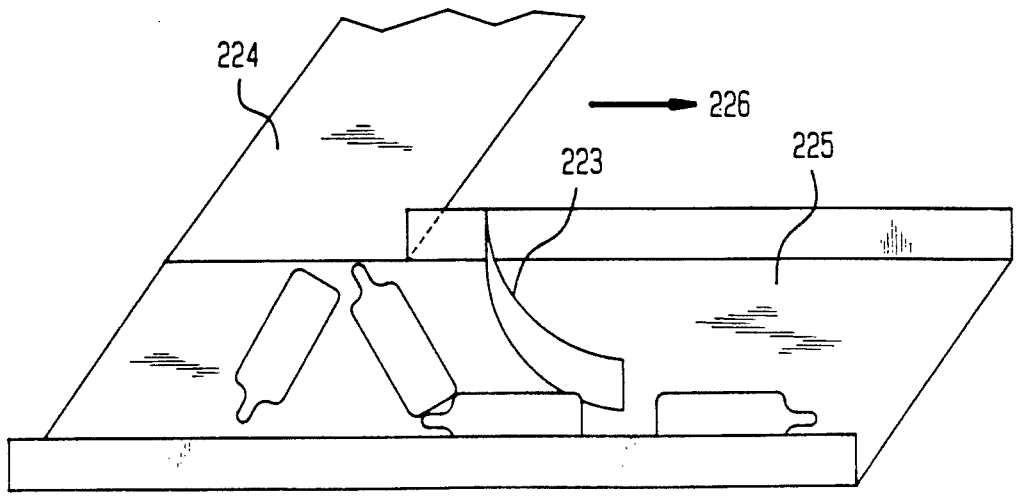
FIG. 8 is a perspective view of the initial conveyor of the bottle feed mechanism.

On the opposite side of inclined conveyor 203 from slide 214 is slide 224. Slide 224 begins beyond space 211, and is inclined to convey bottles from space 211 to an initial conveyor belt 225. As shown in FIG. 8, the initial conveyor belt has walls to prevent bottles from falling off the sides. Downstream of slide 224 is resilient arm 223 which extends from one side of conveyor 225 to a spaced distance from the other side. Initial conveyor belt 225 eventually connects with the main conveyor 2.

In operation of the feed system 200, unsorted plastic bottles for recycling are placed in bin 202. Because the bin is slightly inclined, bottles will tend to gravitate towards inclined conveyor 203. As pulleys 206 move in the rotational direction 207, bottles 230 will fall into the spaces between cleats 205. Most long and thin bottles, such as one or two-liter bottles, will tend to lie on their sides against belt 204', such as bottle 231. Larger bottles, such as one-gallon plastic bottle 232, will be bulkier and may lay in any fashion on the inclined conveyor. However, some long and thin bottles, such as bottle 233, might stand on the inclined conveyor, and extend relatively high above the upper surface of conveyor belt 204.

When bottles 231–233 are conveyed up the conveyor to space 211, they must pass under rotating first paddle wheel 208 before they can reach slide 224 and, eventually, the main conveyor. For example, since the distance between conveyor belt 204 and paddles 212 is slightly greater than the diameter of a standard two liter bottle, bottle 231 would pass under paddle wheel 208, and then fall onto slide 224.

On the other hand, one-gallon bottle 232 would not pass under paddle wheel 208, because the size of bottle 232 is greater than the diameter of a two-liter bottle. Therefore, paddle wheel 212 will knock the bottle off of conveyor 203 and onto slide 214. The bottle will travel down slide 214, until it reaches bottom edge 215 and second paddle wheel 216. Since the distance between second paddle wheel 216 and slide 214 is also only slightly greater than the diameter of a two-liter bottle, the rotating paddle wheel will knock the bottle off slide 214 and into chute 219. The removed bottle will continue down the chute until it reaches other bottles which are larger than the desired size of bottles to be sorted.

A two-liter bottle, such as bottle 233 which is standing upright on conveyor 203, will also be knocked off conveyor 203 and onto slide 214 by first paddle wheel 208. This is because the height of a standard two-liter bottle is greater than the diameter. The bottle will travel down slide 214, until it reaches bottom edge 215 and second paddle wheel 216. However, because slide 214 is smooth and inclined, it is highly probable that bottle 232 would fall on it side as it flies on to the slide under the impetus of first paddle wheel 208. If the bottle is on its side as it approaches second paddle wheel 216, it will pass under the paddle wheel and fall back into bin 202. Thus, even if a two-liter bottle is removed from inclined conveyor 203 one or more times, it will continue to return to bin 202 until it finally passes through space 211 and onto slide 224.

As seen in FIG. 8, bottles which reach slide 224 are deposited on conveyor 225, and travel in direction 226 towards resilient arm 223. Since inclined conveyor 203 should be wide enough to carry more than one bottle against any one cleat 205, the bottles deposited on conveyor 225 may be too close together to be sorted properly when they reach the main conveyor 2. Therefore, resilient arm 223 extends into the conveyor and forces the bottles into a single-file against one side of conveyor 225. Consequently, when the bottles reach conveyor 2, they will be in single file and disposed against only side of conveyor 2.

Although it is not shown, it is preferable to place a series of conveyors of ever increasing speeds between conveyor 225 and conveyor 2. In that way, the distance between individual bottles will be increased as the first bottle is pulled by a faster conveyor while the next bottle is still disposed on the slower conveyor. Further, the series of increasing speed conveyors facilitates the smooth transition of bottles to the high-speed main conveyor 2.

As these and other variations and combinations of the features described above can be utilized without departing from the present invention as defined in the appended claims, the foregoing description of the preferred embodiments should be understood as being illustrative rather than as limiting the invention as defined in the claims.

We claim:

1. A method of sorting bottles for recycling comprising the steps of
   conveying a bottle via a conveying means to a first sensing area, determining whether said bottle is clear while said bottle is in said first sensing area and removing said bottle from said conveying means to a pile of clear bottles if said bottle is clear, and
   if said bottle is not removed in said first sensing area, conveying the bottle via said conveying means to a second, separate sensing area, determining whether said bottle is colored while said bottle is in said second sensing area and removing said bottle from said conveying means to a pile of colored bottles if said bottle is colored.

2. The method of claim 1 further comprising the steps of
   if said bottle is not removed in either said first or said second sensing area, conveying the bottle via said conveying means to a third, separate sensing area, determining whether said bottle is translucent while said bottle is in said third sensing area and removing said bottle from said conveying means to a pile of translucent bottles if said bottle is translucent.

3. The method of claim 1 wherein said step of determining whether said bottle is clear comprises disposing the bottle between a light emitter and a light detector, emitting red light and passing such light through the bottle, and determining if the magnitude of such light has been diminished by passage through the bottle.

4. The method of claim 3 wherein said step of determining whether the bottle is colored includes the steps of determining whether the bottle is of a particular color by emitting a light of a wavelength corresponding to such particular color, passing such light through the bottle and determining if the magnitude of such light has been diminished by passage through the bottle.

5. The method of claim 4 wherein said particular color is green.

6. The method of claim 2 wherein said step of determining whether said bottle is translucent comprises disposing the bottle between a light emitter and a light detector, emitting high intensity red or infrared light and passing such light through the bottle, and determining if the magnitude of such light has been diminished by passage through the bottle.

7. The method of claim 1 or claim 2 further comprising the steps of conveying the bottle via said conveying means to a separate polarization sensing area before the bottle is conveyed to the first, second or third sensing areas, determining whether said bottle is glass, or one or more of a group of materials comprising polyvinyl chloride (PVC) or polyvinylidine chloride (PVDC) while said bottle is in said polarization sensing area and removing said bottle from said conveying means to a pile of glass, PVC or PVDC bottles if said bottle is glass, PVC or PVDC.

8. The method of claim 7 wherein said step of determining whether said bottle is glass or one or more of a group of materials comprising polyvinyl chloride (PVC) or polyvinylidine chloride (PVDC) comprises disposing the bottle between a polarized light emitter and a polarized light detector, emitting polarized light and passing such light through the bottle, and determining whether such light has changed polarization by passage through the bottle.

9. The method of claim 8 wherein said polarized light is circularly polarized light.

10. The method of claim 1 or claim 2 further comprising conveying a bottle via said conveying means to a separate X-ray sensing area before the bottle is conveyed to the first, second or third sensing areas, determining whether said bottle contains chlorine while said bottle is in said X-ray sensing area and removing said bottle from said conveying means to a pile of chlorine-containing bottles if said bottle contains chlorine.

11. The method of claim 10 wherein said step of determining whether said bottle contains chlorine comprises irradiating said bottle with X-rays, determining whether the bottle emits secondary radiation associated with the presence of chlorine upon such irradiation.

12. A method of determining whether plastic bottles for recycling contain chlorine comprising
irradiating the plastic bottles with X-rays, and
detecting any secondary X-ray florescence associated with the presence of chlorine.

13. The method of claim 12 wherein said irradiating step includes the step of conveying a plurality of said plastic bottles along a conveying means to a X-ray sensing area, and irradiating each such bottle with said X-rays while such bottle is in said X-ray sensing area, the method further comprising the step of removing a particular bottle from said conveying means if said secondary X-ray florescence associated with the presence of chlorine is detected while such bottle is in said X-ray sensing area.

14. The method of claim 12 wherein said step of irradiating comprises irradiating said bottles with X-rays of about 6 kiloelectron volts (KEV) energy, and
said step of detecting comprises detecting secondary radiation having energy equal to about 2.8 KEV.

15. The method of claim 14 wherein said irradiating step includes the step of directing X-rays from a sample of Fe-55 to said X-ray sensing area.

16. The method of claim 13 wherein said step of detecting comprises detecting the presence of polyvinyl chloride or polyvinylidine chloride.

17. The method of claim 12 wherein said step of detecting comprises
measuring said second X-ray florescence of said bottles at predetermined intervals of time during said irradiating step such that a plurality of measurements are performed with respect to each bottle, and
signalling that a said bottle contains chlorine if the secondary X-ray fluorescence measured by at least one of said measurements is associated with the presence of chlorine.

18. A method of determining whether bottles are composed of glass, or one or more of a group of materials comprising polyvinyl chloride (PVC) or polyvinylidine chlorine (PVDC) comprising disposing a bottle between a first polarized light emitter and a first polarized light detector,
emitting circularly polarized light and passing such light through the bottle, and
determining whether such light has changed polarization by passage through the bottle.

19. The method of claim 18 further comprising the steps of
conveying one bottle between said emitter and said detector from a line of bottles,
diverting said one bottle from said line of bottles to a pile of glass bottle if the change in polarization indicates said one bottle is glass, and
diverting said one bottle from said line of bottles to a pile of polyvinyl chloride (PVC) or polyvinylidine chloride (PVDC) bottles if the change in polarization indicates said bottle is composed of PVC or PVDC.

20. The method of claim 18 further comprising the steps of
conveying one bottle between said emitter and said detector from a line of bottles,
if the change in polarization indicates said one bottle is glass, diverting said one bottle from said line of bottles to a pile of glass bottles,
if said one bottle is not diverted, disposing said one bottle between a second polarized light emitter and a second polarized light detector, emitting circularly polarized light and passing such light through said one bottle, determining whether such light has changed polarization by passage through the bottle, and diverting said one bottle to a pile of PVC or PVDC bottles if the change in circularly polarized light from said second polarized light emitter indicates said bottle is composed of PVC or PVDC.

21. The method of claims 19 or 20, wherein
said step of emitting polarized light comprises emitting light of random polarization, passing said random light through a linear polarizing filter, and passing the linearly polarized light through a first quarterwave plate to produce said circularly polarized light of a first-handedness, and
wherein said step of determining the change in polarization comprises passing the light exiting the bottle through a second quarterwave plate followed by a second linear polarizing filter, the relative orientation of said second quarter wave plate with respect to said second linear polarizing filter being such to block light that is circularly polarized with said first handedness.

22. The method of claim 19 or 20 further comprising the step of:
emitting nonpolarized light of substantially equivalent wave length to said circularly polarized light through the bottle,
determining the attenuation of said nonpolarized light through the bottle, comparing said change in polarization of said polarized light after passage through said bottle with the attenuation of said nonpolarized light after passage through said bottle.

23. A method of determining the composition of bottles comprising
disposing a bottle between a first polarized light emitter and a first polarized light detector,
emitting circularly polarized light and passing such light through the bottle, and
determining whether such light has changed polarization by passage through the bottle.

* * * * *